United States Patent
Shah et al.

(10) Patent No.: US 12,376,806 B2
(45) Date of Patent: Aug. 5, 2025

(54) DETERMINATION OF METABOLIC RATE FROM STATIC PET SCAN

(71) Applicant: Siemens Medical Solutions USA, Inc., Malvern, PA (US)

(72) Inventors: Vijay Shah, Knoxville, TN (US); Sven Zuehlsdorff, Oak Brook, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 653 days.

(21) Appl. No.: 17/309,595

(22) PCT Filed: Oct. 22, 2019

(86) PCT No.: PCT/US2019/057308
§ 371 (c)(1),
(2) Date: Jun. 9, 2021

(87) PCT Pub. No.: WO2020/146032
PCT Pub. Date: Jul. 16, 2020

(65) Prior Publication Data
US 2022/0015721 A1     Jan. 20, 2022

Related U.S. Application Data (60) Provisional application No. 62/788,973, filed on Jan. 7, 2019.

(51) Int. Cl.
*G16H 50/20*     (2018.01)
*A61B 6/00*     (2024.01)
(Continued)

(52) U.S. Cl.
CPC .............. *A61B 6/037* (2013.01); *A61B 6/50* (2013.01); *A61B 6/5217* (2013.01); *A61B 6/5294* (2013.01); *G16H 50/20* (2018.01)

(58) Field of Classification Search
None
See application file for complete search history.

(56) References Cited

U.S. PATENT DOCUMENTS

| | | |
|---|---|---|
| 6,628,982 B1 | 9/2003 | Thomas et al. |
| 9,872,664 B1 | 1/2018 | Jin et al. |

(Continued)

FOREIGN PATENT DOCUMENTS

| | | |
|---|---|---|
| CN | 103260521 | 8/2013 |
| CN | 104463840 | 3/2015 |

(Continued)

OTHER PUBLICATIONS

Zanotti-Fregonara, et al., "Image-derived input function for brain PET studies: many challenges and few opportunities", Journal of Cerebral Blood Flow & Metabolism (2011) 31, 1986-1998 (Year: 2011).*

(Continued)

*Primary Examiner* — Christopher Koharski
*Assistant Examiner* — Farouk A Bruce (57) ABSTRACT

A system and method include identification of a blood pool region of the body based on the acquired positron emission tomography data, determination of activity in the blood pool region associated with a first time based on the acquired positron emission tomography data, determination of a scale factor based on the determined activity in the blood pool region and on an input function associated with one or more other human bodies, determination of activity in a tissue region associated with a second time based on the acquired positron emission tomography data, determination of a specific uptake ratio associated with the second time based on the activity in the tissue region, the scale factor and a value of the input function at the second time, determination of an estimate of metabolic rate in the tissue region based on the specific uptake ratio and the input function, and deter- (Continued)

mination of a diagnosis associated with the tissue region based on the estimate of metabolic rate.

20 Claims, 6 Drawing Sheets

(51) Int. Cl.
*A61B 6/03* (2006.01)
*A61B 6/50* (2024.01)

(56) References Cited

U.S. PATENT DOCUMENTS

| | | | |
|---|---|---|---|
| 2005/0215889 | A1 | 9/2005 | Patterson |
| 2008/0033291 | A1 | 2/2008 | Rousso et al. |
| 2009/0018438 | A1 | 1/2009 | Schroder et al. |
| 2009/0024547 | A1* | 1/2009 | Lu .................. G16C 20/30 |
| | | | 706/21 |
| 2009/0175418 | A1 | 7/2009 | Sakurai et al. |
| 2015/0342552 | A1 | 12/2015 | Black |
| 2016/0158391 | A1 | 6/2016 | Blaha |
| 2016/0228056 | A1 | 8/2016 | Hooker et al. |

FOREIGN PATENT DOCUMENTS

| | | |
|---|---|---|
| CN | 105025779 | 11/2015 |
| CN | 105979872 | 9/2016 |
| CN | 107661115 | 2/2018 |
| CN | 108836375 | 11/2018 |

OTHER PUBLICATIONS

Lee et al., "Extraction of an input function from dynamic micro-PET images using wavelet packet based sub-band decomposition independent component analysis", NeuroImage 63 (2012) pp. 1273-1284 (Year: 2012).*

Patlak, Clifford S., "Graphical Evaluation of Blood-to-Brain Transfer Constants from Multiple-Time Uptake Data", Journal of Cerebral Blood Flow and Metabolism, 3:1-7, 1983, Raven Press, New York, 7 pp.

Thie, Joseph A., "Clarification of a Fractional Uptake Concept", The Journal of Nuclear Medicine, 36:711-712, 1995, 3 pp.

Hofheinz, Frank, "Comparative evaluation of SUV, tumor-to-blood standard uptake ratio (SUR), and dual time point measurements for assessment of the metabolic uptake rate in FDG PET", EJNMMI Research, 6:53, 2016, 9 pp.

Kotasidis, et al., "Advanced kinetic modelling strategies: towards adoption in clinical PET imaging," Clinical and Translational Imaging, vol. 2, No. 3, Jun. 1, 2014, pp. 219-237.

International Search Report for Corresponding PCT Appln No. PCT/US2019/057308, mailed Jan. 7, 2020.

Liu Li, Yu Chun-Jing et al; "The new method of PET/CT molecular imaging kinetic modeling in the diagnosis of lung cancer"; published: Apr. 15, 2015.

Sun, Tao et al; "Imaging Theory, Predominance and Clinical Applications of PET/CT"; Chinese Journal of Medical Physics; published: Jan. 31, 2010; vol. 27; No. 1.

Karantanis, D. et al; "Oncologic PET/CT interpretation and reporting approaches"; published: Dec. 31, 2014; DOI: 10.3413/Nukmed-0613-13-07.

Van Den Hoff, Jörg et al; "The PET-derived tumor-to-blood standard uptake ratio (SUR) is superior to tumor SUV as a surrogate parameter of the metabolic rate of FDG"; published: Nov. 23, 2013.

* cited by examiner

DETERMINATION OF METABOLIC RATE FROM STATIC PET SCAN

CROSS-REFERENCE TO RELATED APPLICATIONS

The present application is related to and claims priority to U.S. Provisional Patent Application No. 62/788,973, filed Jan. 7, 2019, the contents of which are incorporated by reference in their entirety, for all purposes.

BACKGROUND

According to conventional nuclear imaging, a radiopharmaceutical tracer is introduced into a patient body by injection or ingestion. The radiopharmaceutical tracer emits gamma rays (in the case of single-photon-emission-computer-tomography (SPECT) imaging) or positrons which annihilate with electrons to produce gamma rays (in the case of positron-emission-tomography (PET) imaging). A detector system located outside the body detects the emitted gamma rays and reconstructs images based thereon.

Gamma ray emission may depend in part on the metabolic rate of the tissue in which the radiopharmaceutical tracer resides. Accordingly, images acquired using nuclear imaging may represent metabolic rate. For example, a standardized uptake value (SUV) image, which may be determined based on a PET image, provides a semi-quantitative measure of tracer uptake in a region of interest. The SUV image normalizes tissue activity to the injected activity and to a measure of the volume of distribution (e.g., total body weight or lean body mass). Since the values of an SUV image depend on the time post-injection at which the PET image was acquired, an SUV image is not considered a suitably-accurate proxy for metabolic rate.

The specific uptake ratio (SUR) is a ratio of an SUV image of patient tissue to an SUV image of a blood pool region of the patient. The fractional uptake rate (i.e., a surrogate for the metabolic rate) may be determined from the SUR. Although the SUR does not exhibit the post-injection time dependency of an SUV image, the SUR fails to take blood glucose into account. Accordingly, an accurate determination of SUR (and of the fractional uptake rate) requires periodic post-injection arterial blood sampling.

Parametric PET (dynamic) scans produce data from which metabolic rate can be determined. However, parametric PET scans are not commonly available. Even where available, parametric PET scans require a significantly longer scan time than a conventional static PET scan and therefore do not conform to typical clinical protocols.

Systems are desired to provide an estimation of tissue metabolic rate based on a static PET scan.

DETAILED DESCRIPTION

The following description is provided to enable any person in the art to make and use the described embodiments and sets forth the best mode contemplated for carrying out the described embodiments. Various modifications, however, will remain apparent to those in the art.

Generally, some embodiments provide an estimation of tissue metabolic rate based on a static PET scan. Such an estimation may be provided by scanning body regions over time using a PET scanner. A blood pool region of the body (e.g., the descending aorta) and an area of interest (e.g., a tumor) are identified based on the PET data of a body over a scan time. A scale factor is determined based on activity in the blood pool region at the time of scanning the blood pool region and on a population-based input function. Next, a SUR at the time of scanning the tumor is determined based on activity in the tumor at the tumor scanning time, the scale factor, and the value of the population-based input function at the tumor scanning time. An estimate of metabolic rate (e.g., a pseudo-Fractional Uptake Rate (pFUR)) in the tumor is then determined based on the SUR and the population-based input function.

Embodiments may therefore provide efficient estimation of metabolic rate without requiring parametric PET scans or blood sampling. In some embodiments, the estimated rate may be used to evaluate the tumor (e.g., determine a diagnosis).

Figure 1:
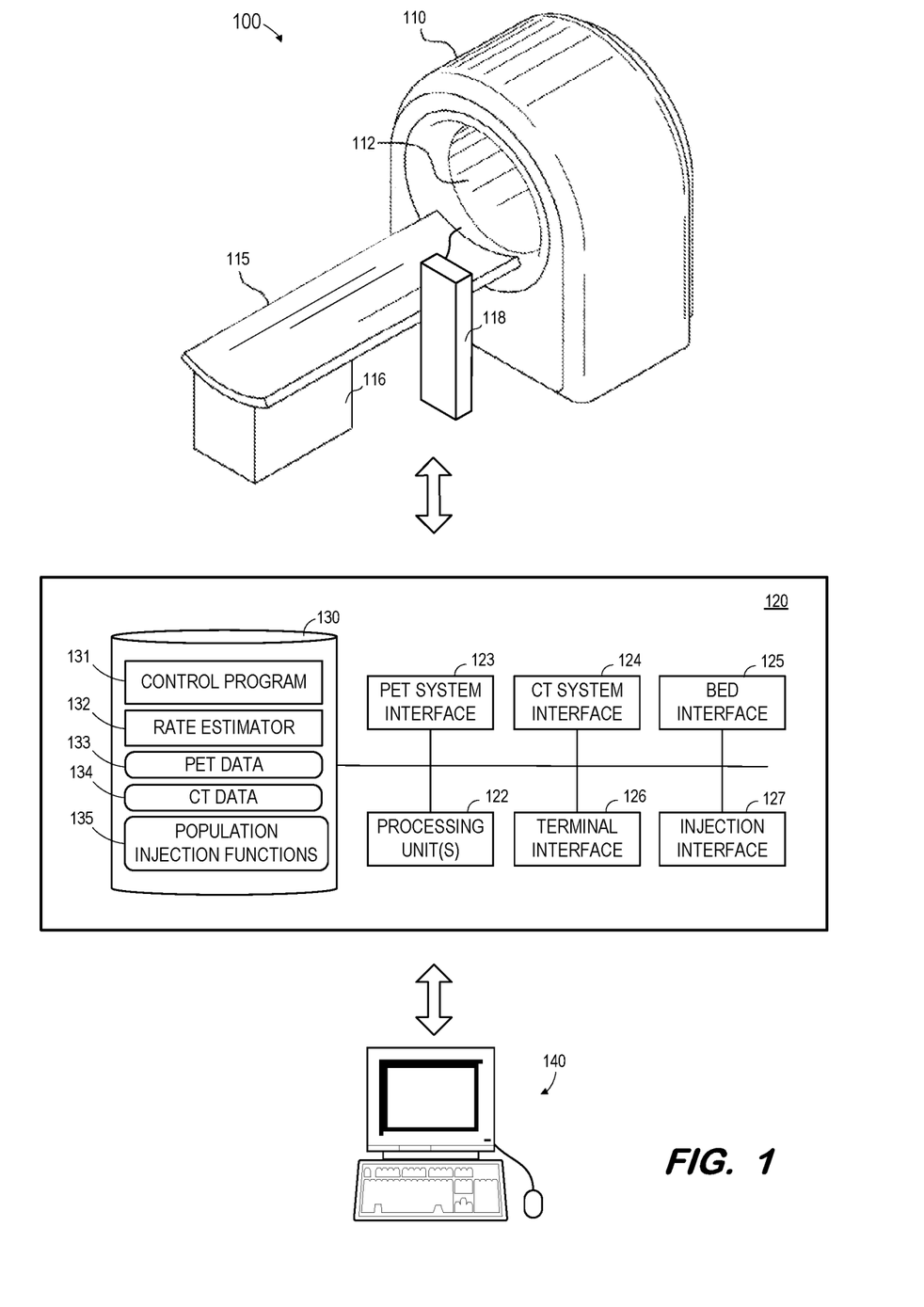
FIG. 1 is a block diagram of a PET/CT imaging system according to some embodiments.

FIG. 1 illustrates PET/CT system 100 to execute one or more of the processes described herein. Embodiments are not limited to system 100.

According to conventional PET imaging, a tracer compound including a radionuclide is introduced into a patient body by injection or ingestion. Radioactive decay of the radionuclide generates positrons, which eventually encounter electrons and are annihilated thereby. Annihilation produces two gamma photons which travel in approximately opposite directions. Accordingly, an annihilation event, or prompt, is identified when two detectors disposed on opposite sides of the body detect the arrival of two oppositely-travelling gamma photons within a particular coincidence time window.

Because the two gamma photons travel in approximately opposite directions, the locations of the two detectors determine a Line-of-Response (LOR) along which the annihilation event occurred. Each annihilation event may be represented by raw (i.e., list-mode) data specifying the three-dimensional position and the time at which the event occurred. Time-of-flight (TOF) PET additionally measures the difference between the detection times of the two gamma photons arising from the annihilation event. This difference may be used to estimate a particular position along the LOR at which the annihilation event occurred.

System 100 includes gantry 110 defining bore 112. As is known in the art, gantry 110 houses PET imaging components for acquiring PET image data and CT imaging components for acquiring CT image data. The CT imaging components may include one or more x-ray tubes and one or more corresponding x-ray detectors as is known in the art.

The PET imaging components may include any number or type of detectors (e.g., silicon photo-multipliers (SiPM) or photo-multiplier tubes (PMT) in any configuration as is known in the art. The detectors are associated with a slice thickness (spatial resolution) such that the components are capable of independently imaging two slices separated by a distance greater than or equal to the slice thickness. The slice thickness (e.g., 2.0 mm) corresponds to resolution of the detectors.

Injection system 118 may operate to deliver calibrated injections of fluorodeoxyglucose (FDG), iodine, or other radiopharmaceuticals to a patient before and/or during a PET scan. In some embodiments, injection system 118 is incorporated into gantry 110. Injection system 118 may support a wired or wireless communications link with control system 120 for receiving information specifying dosage, injection protocol and scan delay.

Bed 115 and base 116 are operable to move a patient lying on bed 115 into and out of bore 112 before, during and after imaging. In some embodiments, bed 115 is configured to translate over base 116 and, in other embodiments, base 116 is movable along with or alternatively from bed 115.

Movement of a patient into and out of bore 112 may allow scanning of the patient using the CT imaging elements and the PET imaging elements of gantry 110. Such scanning may proceed based on scanning parameters such as scan ranges and corresponding scanning speeds. Bed 115 and base 116 may provide continuous bed motion and/or step-and-shoot motion during such scanning according to some embodiments.

Control system 120 may comprise any general-purpose or dedicated computing system. Accordingly, control system 120 includes one or more processing units 122 configured to execute processor-executable program code to cause system 120 to operate as described herein, and storage device 130 for storing the program code. Storage device 130 may comprise one or more fixed disks, solid-state random-access memory, and/or removable media (e.g., a thumb drive) mounted in a corresponding interface (e.g., a USB port).

Storage device 130 stores program code of control program 131. One or more processing units 122 may execute control program 131 to, in conjunction with PET system interface 123, bed interface 125, and injection interface 127, control hardware elements to inject a radiopharmaceutical into a patient, move the patient into bore 112 past PET detectors of gantry 110, and detect coincidence events occurring within the patient. The detected events may be stored in memory 130 as PET data 133, which may comprise list-mode data and/or sinograms.

One or more processing units 122 may also execute control program 131 to, in conjunction with CT system interface 124, cause a radiation source within gantry 110 to emit radiation toward a body within bore 112 from different projection angles, and to control a corresponding detector to acquire two-dimensional CT data. The CT data may be acquired substantially contemporaneously with the PET data as described above, and may be stored as CT data 134. Such CT data 134 may be used for attenuation correction of contemporaneously-acquired PET data 133 as is known in the art. In this regard, control program 131 may also be executed to reconstruct PET data 133 of a PET scan into three-dimensional slices using any reconstruction algorithm that is or becomes known.

Storage device 130 also includes rate estimator program 132 for estimating metabolic rate of an imaged region according to some embodiments. As mentioned above and described in detail below, such rate estimation utilizes previously-acquired population injection functions 135.

PET images, CT images and/or estimated metabolic rate may be transmitted to terminal 140 via terminal interface 126. Terminal 140 may comprise a display device and an input device coupled to system 120. Terminal 140 may display the PET images, CT images, and/or estimated metabolic rate. Terminal 140 may receive user input for controlling display of the data, operation of system 100, and/or the processing described herein. In some embodiments, terminal 140 is a separate computing device such as, but not limited to, a desktop computer, a laptop computer, a tablet computer, and a smartphone.

Each component of system 100 may include other elements which are necessary for the operation thereof, as well as additional elements for providing functions other than those described herein. Each functional component described herein may be implemented in computer hardware, in program code and/or in one or more computing systems executing such program code as is known in the art. Such a computing system may include one or more processing units which execute processor-executable program code stored in a memory system.

Figure 2:
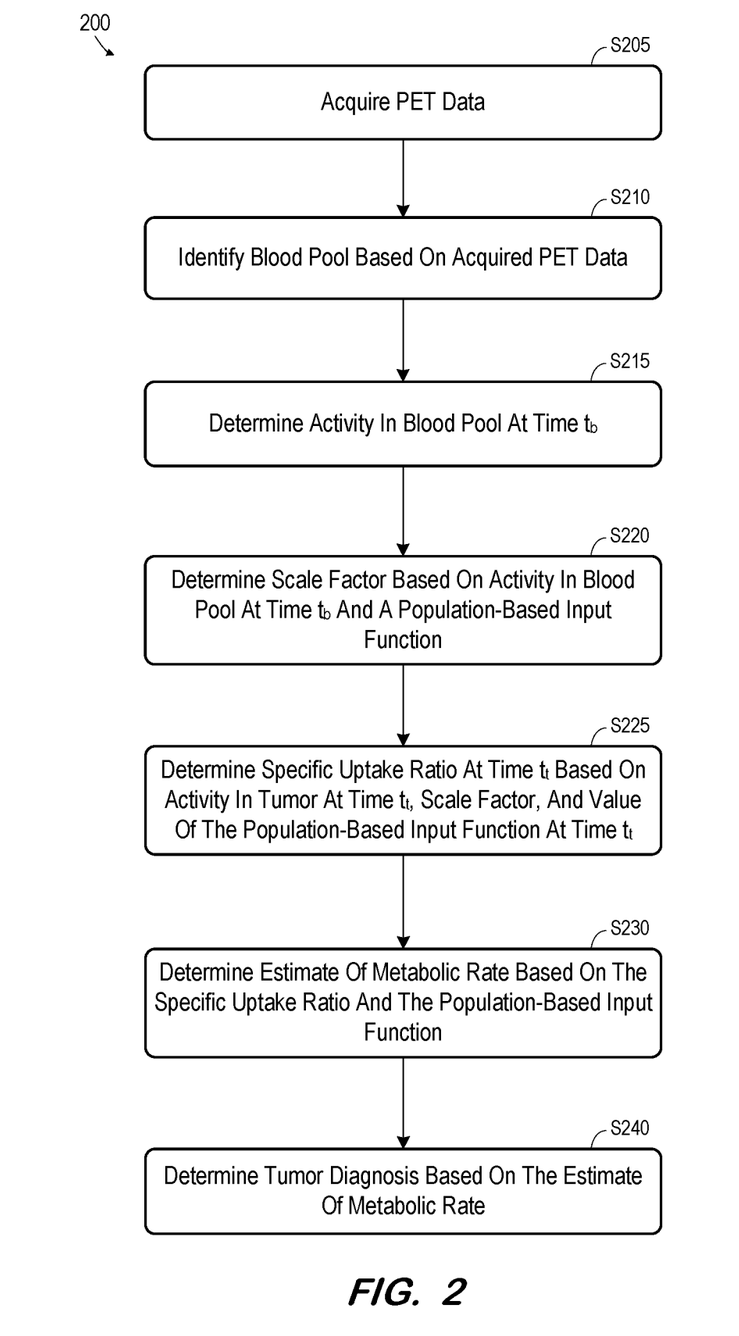
FIG. 2 comprises a flow diagram of a process to estimate metabolic rate of tissue based on a static PET scan according to some embodiments.

FIG. 2 comprises a flow diagram of process 200 to estimate metabolic rate based on a PET scan according to some embodiments. Flow diagram 200 and other processes described herein may be executed using any suitable combination of hardware and software. Software program code embodying these processes may be stored by any non-transitory tangible medium, including a fixed disk, a volatile or non-volatile random-access memory, a DVD, a Flash drive, and a magnetic tape. Embodiments are not limited to the examples described below.

PET data is initially acquired at S205. The PET data may be acquired by a conventional static PET scan after injection of a radioactive tracer into a subject volume (e.g., a patient) as is known in the art. The acquired PET data may comprise, in some embodiments, list-mode PET data as described above. The PET data may be acquired by an imaging system separate from a system to perform the remainder of process 200. For example, the PET data may be originally acquired in an imaging theatre, with process 200 being executed by a separate system in a separate location hours, days, months, etc. after the acquisition.

According to some embodiments, the data acquired by a PET scanner is formatted into sinograms. A sinogram is a data array of the angle versus the displacement of each LOR. Each sinogram stores the location of the LOR of each coincidence event such that all the LORs passing through a single point in the volume trace a sinusoid curve in the sinogram. Each sinogram includes one row containing the LOR for a particular azimuthal angle $\varphi$. Each of such rows corresponds to a one-dimensional parallel projection of the tracer compound distribution at a different coordinate.

Figure 3:
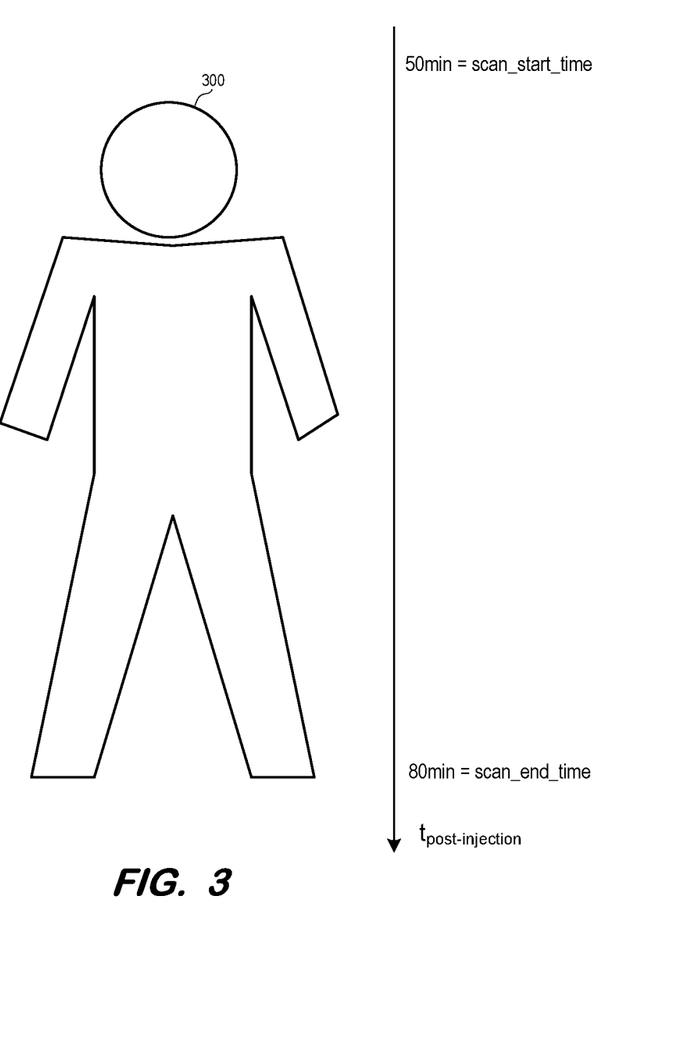
FIG. 3 illustrates performance of a PET scan according to some embodiments.

FIG. 3 illustrates acquisition of PET data over time according to some embodiments. The arrow represents the passage of time after injection of the radiopharmaceutical, with respect to regions of body 300 from which PET data is acquired during the illustrated time periods. As shown, acquisition of the PET data (i.e., scanning of body 300) begins after 50 minutes have passed post-injection. Embodiments are not limited to the specific timing examples provided herein.

With reference to FIG. 1, movement of body 300 into bore 112 may begin at the 50 minute mark (i.e., scan start time=50 min). Body 300 is then moved continuously past the PET detectors of gantry 110 until the entire body has passed by the detectors at around the 80 minute mark (i.e., scan end time=80 min). Accordingly, PET data (e.g., gamma photons) are received from different regions of the body at different times post-injection. As mentioned above, the PET data may be reconstructed into three-dimensional slices. Since the acquired PET data is associated with a particular time at which the PET data was acquired, each image slice reconstructed therefrom may also be associated with an acquisition time. In one example, an image slice of a head region of body 300 may be associated with an acquisition time of 55 minutes post-injection, while an image slice of a chest region of body 300 may be associated with an acquisition time of 65 minutes post-injection.

A blood pool region is identified at S210 based on the acquired PET data. Identification of a blood pool region may include identification of an easily-visible blood region (e.g., the descending aorta) in the PET data, and derivation of the blood pool region via segmentation of the entire descending aorta or by defining a cylinder or other three-dimensional volume based on a point within the identified blood region.

Figure 4:
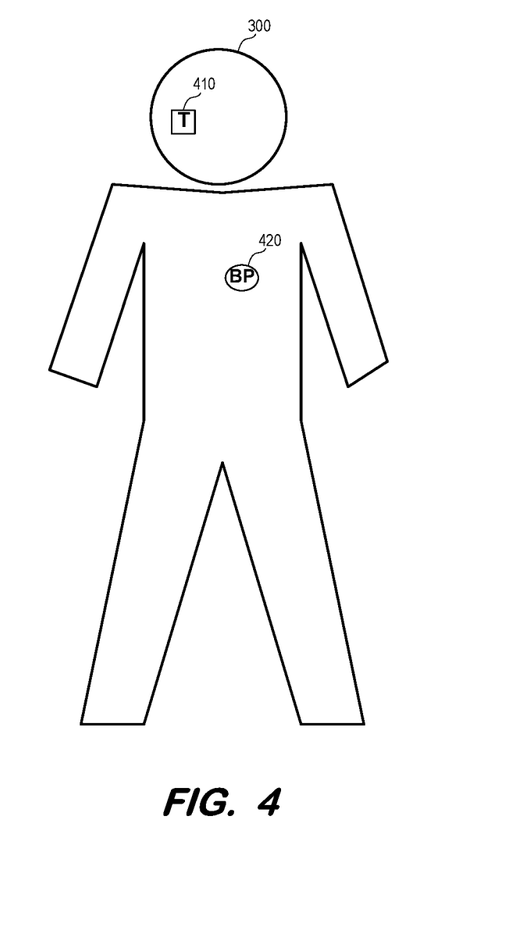
FIG. 4 illustrates locations of blood pool and tumor regions within a PET image according to some embodiments.

FIG. 4 depicts blood pool region 420 identified within body 300 based on acquired PET data according to the present example. Also shown in FIG. 4 is tumor area 410, within which metabolic rate is to be estimated according to the present example. Embodiments may provide estimation of metabolic rate within any region of body 400.

Figure 5:
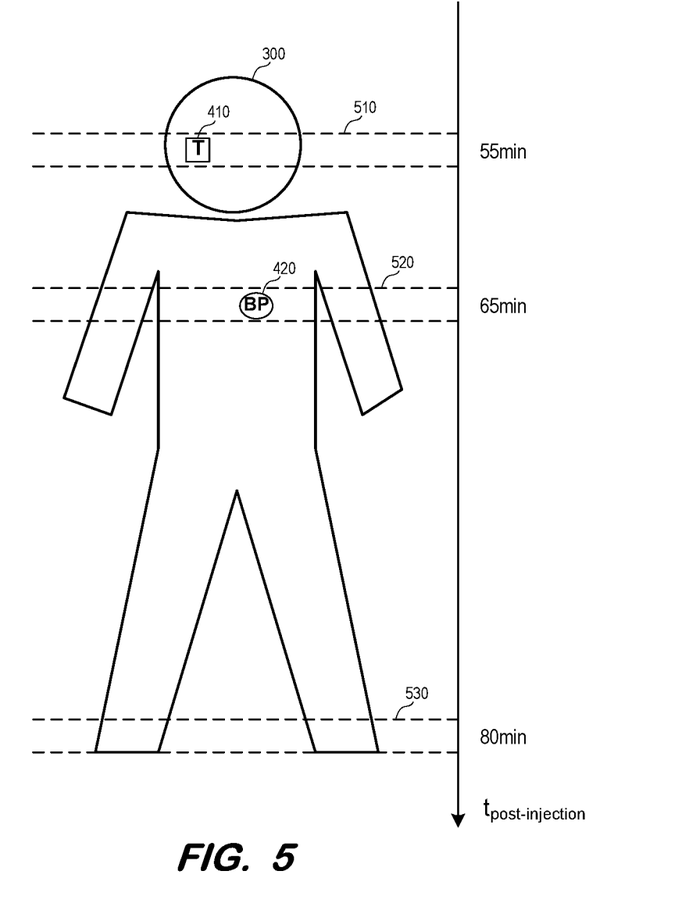
FIG. 5 illustrates slice acquisition times corresponding to blood pool and tumor regions according to some embodiments.

Activity within the blood pool region is determined at S215. The determined activity is associated with time $t_b$, which is the time at which the PET data (i.e., gamma photons) was acquired from the blood pool region. FIG. 5 illustrates the acquisition time (i.e., 65 min post-injection) associated with slice 520 including blood pool region 420 according to the present example. FIG. 5 also shows acquisition times associated with slice 510 including tumor region 410 (i.e., 55 min) and with slice 530 including the lower extremities of body 300 (i.e., 80 min).

Returning to process 300, a scale factor is determined at S220 based on the activity determined at S215 and on a population-based input function. The population-based input function may comprise a previously-determined input function which models the decay of radiopharmaceutical within a body. The population-based input function may be calculated based on prior blood sampling of one or more patients, and may be selected from several stored population-based input functions. The selected population-based input function may have been calculated under conditions which best match those of the present acquisition (e.g., patient size, patient weight, patient age, injected pharmaceutical, dosage, and/or injection rate).

According to some embodiments, the scale factor is determined as:

$$S = \frac{T * C_b(t_b)}{\int_{scan\_start\_time}^{scan\_end\_time} C_{popIF}(t)}$$

where $C_b(t_b)$ is determined in units of SUV from the PET data of the blood pool region acquired at time $t_b$ as is known in the art, $C_{popIF}(t_b)$ is the activity indicated by the population-based input function at time $t_b$, and T is the total time duration from scan start time to scan end time. With respect to the present example, $$S = \frac{30 * C_b(65)}{\int_{50}^{80} C_{popIF}(t)}$$

Next, at S225, an SUR at time $t_t$ is determined. Time $t_t$ is the time at which the PET data of the region of interest (e.g., region 410) was acquired. The region of interest is the region for which the metabolic rate is to be estimated. The SUR at time $t_t$ may be determined at S225 based on the activity in the region of interest (e.g., the tumor) at time $t_t$, the previously-computed scale factor S, and the value of the population-based input function at time $t_t$. According to some embodiments, $$C_b(t_t) = S * C_{popIF}(t_t)$$

and SUR($t_t$) may be determined as:

$$SUR(t_t) = \frac{C_t(t_t)}{C_b(t_t)}$$

where $C_t(t_t)$ is the activity in the region of interest at time $t_t$ ($t_t$=55 minutes in the present example).

An estimate of metabolic rate in the region of interest is then determined at S230. The estimate may be determined based on the SUR determined at S225 and the population-based input function. In this regard, the Patlak equation provides:

$$SUR(t_t) = \frac{C_t(t_t)}{C_b(t_t)} = K_m \times \frac{\int_0^{t_t} C_b(s)ds}{C_b(t_t)} + V_d$$

where $K_m$ is the metabolic rate and $V_d$ is the apparent volume of distribution. Estimating $C_b(t_t) \approx S*C_{popIF}(t_t)$ and $\int_0^{t_t} C_b(s)ds \approx S*\int_0^{t_t} C_{popIF}(s)ds$ in the Patlak equation:

$$K_m \approx \frac{SUR(t_t) - V_d}{\int_0^{t_t} C_{popIF}(s)ds / C_{popIF}(t_t)} \approx pFUR$$

where pFUR is an estimate of metabolic rate referred to as the pseudo Fraction Uptake Rate.

All terms of the above equation are known except for $V_d$. $V_d$ may be modeled or otherwise estimated as is known in the art. In the case of a large $t_t$, $V_d$ may be estimated as equal to 0. Accordingly, pFUR may be determined based solely on $C_b(t_b)$, $C_t(t_t)$ and the population-based input function, without the need for blood samples or a parametric PET scan.

A diagnosis of the region of interest may be determined at S240 based on the estimated metabolic rate within the region of interest. The diagnosis may be determined by an oncologist based on the estimated metabolic rate and on other available data such as but not limited to images acquired using one or more imaging modalities, tissue samples, patient symptoms and patient history.

According to some embodiments, the diagnosis is determined at least in part using a trained neural network. For example, a neural network may be trained to output a diagnosis (e.g., a respective probability for each of a set of possible diagnoses) in response to receiving an estimate of metabolic rate calculated as described above. The input to the neural network may include additional data, such as images, an identifier of the region of interest (e.g., brain, liver), and other physiological data. Such a neural network may be trained as is known in the art based on a set of ground truth diagnoses, each of which is associated with an estimated metabolic rate and any other information to be input to the neural network as described above.

Figure 6:
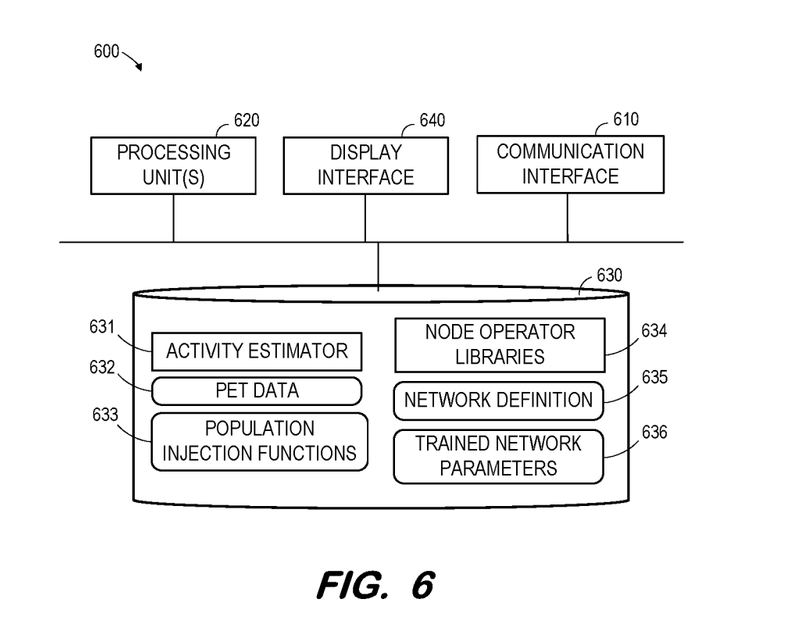
FIG. 6 illustrates a system for determining a diagnosis based on estimated metabolic rate according to some embodiments.

FIG. 6 illustrates computing system 600 according to some embodiments. System 600 may comprise a computing system to implement a trained neural network for determination of a diagnosis based on estimated metabolic rate determined as described above. Computing system 600 may comprise a standalone system, or one or more elements of computing system 600 may be located in the cloud.

System 600 includes communication interface 610 to communicate with external devices via, e.g., a network connection. Processing unit(s) 620 may comprise one or more processors, processor cores, or other processing units to execute processor-executable process steps. In this regard, storage system 630, which may comprise one or more memory devices (e.g., a hard disk drive, a solid-state drive), stores processor-executable process steps of rate estimator 631 which may be executed by processing unit(s) 620 to determine estimated metabolic rate based on PET data 632 and population injection functions 633 as described herein.

Network definition 635 and trained network parameters 636 may define a neural network trained to generate a diagnosis as described above. Network definition 635 may specify any suitable network structure including one or more types of neural networks. Node operator libraries 634 may include code to execute various operations associated with nodes of the defined network.

In operation according to some embodiments, code of rate estimator 631 is executed to determine estimated metabolic rate within a tissue region based on PET data 632 acquired from the region and from an associated blood pool region. As described above, the determination is also based on one of population injection functions 633. The estimated metabolic rate is input to a neural network defined by network definition 635 and trained network parameters 636. Operations of node operator libraries 634 corresponding to the nodes of the defined network are executed in order to generate a network output. The output may comprise a classification network output, which includes a probability associated with each of a set of possible diagnoses.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
an imaging device to:
acquire positron emission tomography data associated with a first human body;
a processing system to:
identify a blood pool region of the first human body based on the acquired positron emission tomography data;
determine activity in the blood pool region associated with a first time based on the acquired positron emission tomography data;
determine an input function which models the decay of a radiopharmaceutical within one or more human bodies different from the first human body;
determine a scale factor based on a ratio of the determined activity in the blood pool region to a value of the input function over time;
determine activity in a tissue region of the first human body associated with a second time based on the acquired positron emission tomography data;
determine a specific uptake ratio associated with the second time based on the determined activity in the tissue region, the scale factor and a value of the input function at the second time; and
determine an estimate of metabolic rate in the tissue region based on the specific uptake ratio and the input function which models the decay of the radiopharmaceutical.

2. A system according to claim 1, wherein determination of activity in the blood pool region associated with the first time is based on positron emission tomography data acquired at the first time and indicating gamma photon emissions within the blood pool region at the first time, and
wherein determination of activity in the tissue region associated with the second time is based on positron emission tomography data acquired at the second time and indicating gamma photon emissions within the tissue region at the second time.

3. A system according to claim 2, wherein determination of the estimate comprises estimation of an apparent volume of distribution.

4. A system according to claim 3, wherein the processing system is configured to reconstruct the acquired data into a plurality of three-dimensional slices,
wherein determination of activity in the blood pool region comprises identification of a first slice of the plurality of three-dimensional slices including the blood pool region and determination that the first slice is associated with the first time, and
wherein determination of activity in the tissue region comprises identification of a second slice of the plurality of three-dimensional slices including the tissue region and determination that the second slice is associated with the second time.

5. A system according to claim 1, wherein determination of the estimate comprises estimation of an apparent volume of distribution.

6. A system according to claim 1, wherein the processing system is configured to determine diagnosis by inputting the estimate into a neural network.

7. A system according to claim 1, wherein determination of the scale factor comprises determination of a second ratio of the determined activity in the blood pool region to an integrated value of the input function from a scan start time to a scan end time, and
wherein determination of the specific uptake ratio is based on the activity in the tissue region at the second time, the scale factor, the value of the input function at the second time, and an integrated value of the input function from the injection time to the second time.

8. A method comprising:
acquiring positron emission tomography data associated with a first human body;
identifying a blood pool region of the first human body based on the acquired positron emission tomography data;
determining activity in the blood pool region associated with a first time based on the acquired positron emission tomography data;
determining an input function which models the decay of a radiopharmaceutical within one or more human bodies different from the first human body;
determining a scale factor based on a ratio of the determined activity in the blood pool region to a value of the input function over time;

determining activity in a tissue region of the first human body associated with a second time based on the acquired positron emission tomography data;

determining a specific uptake ratio associated with the second time based on the activity in the tissue region, the scale factor and a value of the input function at the second time; and determining an estimate of metabolic rate in the tissue region based on the specific uptake ratio and the input function which models the decay of the radiopharmaceutical.

9. A method according to claim 8, wherein determining activity in the blood pool region associated with the first time is based on positron emission tomography data acquired at the first time and indicating gamma photon emissions within the blood pool region at the first time, and wherein determining activity in the tissue region associated with the second time is based on positron emission tomography data acquired at the second time and indicating gamma photon emissions within the tissue region at the second time.

10. A method according to claim 9, wherein determining the estimate comprises estimating an apparent volume of distribution.

11. A method according to claim 10, further comprising:
reconstructing the acquired data into a plurality of three-dimensional slices, wherein determining activity in the blood pool region comprises identifying a first slice of the plurality of three-dimensional slices including the blood pool region and determining that the first slice is associated with the first time, and wherein determining activity in the tissue region comprises identifying a second slice of the plurality of three-dimensional slices including the tissue region and determining that the second slice is associated with the second time.

12. A method according to claim 8, wherein determining the estimate comprises estimating an apparent volume of distribution.

13. A method according to claim 8, further comprising determining a diagnosis by inputting the estimate into a neural network.

14. A method according to claim 8, wherein determining the scale factor comprises determining a second ratio of the determined activity in the blood pool region to an integrated value of the input function from a scan start time to a scan end time, and wherein determining the specific uptake ratio is based on the activity in the tissue region at the second time, the scale factor, the value of the input function at the second time, and an integrated value of the input function from the injection time to the second time.

15. A computing system comprising:
a memory storing processor-executable process steps;
a processing unit to execute the processor-executable process steps to:
acquire positron emission tomography data associated with a first human body;
identify a blood pool region of the first human body based on the acquired positron emission tomography data;

determine activity in the blood pool region associated with a first time based on the acquired positron emission tomography data;

determine an input function which models the decay of a radiopharmaceutical within one or more human bodies different from the first human body;

determine a scale factor based on a ratio of the determined activity in the blood pool region to a value of the input function over time;

determine activity in a tissue region of the first human body associated with a second time based on the acquired positron emission tomography data;

determine a specific uptake ratio associated with the second time based on the activity in the tissue region, the scale factor and a value of the input function at the second time; and determine an estimate of metabolic rate in the tissue region based on the specific uptake ratio and the input function which models the decay of a radiopharmaceutical.

16. A computing system according to claim 15, wherein determination of activity in the blood pool region associated with the first time is based on positron emission tomography data acquired at the first time and indicating gamma photon emissions within the blood pool region at the first time, and wherein determination of activity in the tissue region associated with the second time is based on positron emission tomography data acquired at the second time and indicating gamma photon emissions within the tissue region at the second time.

17. A computing system according to claim 16, wherein determination of the estimate comprises estimation of an apparent volume of distribution.

18. A computing system according to claim 17, the processing unit to execute the processor-executable process steps to:
reconstruct the acquired data into a plurality of three-dimensional slices, wherein determination of activity in the blood pool region comprises identification of a first slice of the plurality of three-dimensional slices including the blood pool region and determination that the first slice is associated with the first time, and wherein determination of activity in the tissue region comprises identification of a second slice of the plurality of three-dimensional slices including the tissue region and determination that the second slice is associated with the second time.

19. A computing system according to claim 15, wherein determination of the estimate comprises estimation of an apparent volume of distribution.

20. A computing system according to claim 15, wherein determination of the scale factor comprises determination of a second ratio of the determined activity in the blood pool region to an integrated value of the input function from a scan start time to a scan end time, and wherein determination of the specific uptake ratio is based on the activity in the tissue region at the second time, the scale factor, the value of the input function at the second time, and an integrated value of the input function from the injection time to the second time.

* * * * *